United States Patent [19]

Herzog et al.

[11] Patent Number: 5,228,177
[45] Date of Patent: Jul. 20, 1993

[54] SAMPLE PREPARATION SYSTEM FOR IRON AND STEEL SAMPLES

[75] Inventors: Helga Herzog, Wallenhorst; Günther Hawickhorst, Bramsche, both of Fed. Rep. of Germany

[73] Assignee: Herzog Maschinenfabrik GmbH & Co., Osnabruck, Fed. Rep. of Germany

[21] Appl. No.: 793,425
[22] PCT Filed: Mar. 3, 1990
[86] PCT No.: PCT/EP90/00359
§ 371 Date: Dec. 13, 1991
§ 102(e) Date: Dec. 13, 1991
[87] PCT Pub. No.: WO91/14166
PCT Pub. Date: Sep. 19, 1991
[51] Int. Cl.⁵ .................. B23P 23/04; G01N 1/32
[52] U.S. Cl. .................. 29/33 R; 51/5 R; 73/864.91
[58] Field of Search .......... 29/33 R, 428, 33 P, 29/563, 564; 73/864.41, 864.44, 864.91, 964.59, 864.58, 864.53, DIG. 9, 864.31, 863; 51/5 R, 5 C, 326, 165.8, 131.1, 237 R, 273, 217 R

[56] References Cited

U.S. PATENT DOCUMENTS

| H361 | 11/1987 | Goodwin | 51/326 |
| 4,541,292 | 9/1985 | Clay | 73/864.59 |
| 4,873,792 | 10/1989 | Linke et al. | 51/165.8 |
| 4,895,033 | 1/1990 | Voss et al. | 73/864.91 |

FOREIGN PATENT DOCUMENTS

| 3344944 | 6/1985 | Fed. Rep. of Germany | 29/33 R |
| 3722180 | 1/1989 | Fed. Rep. of Germany | 29/33 R |
| 2406822 | 5/1979 | France | 29/33 R |
| 59-60241 | 4/1984 | Japan | 29/33 R |

Primary Examiner—William Briggs
Attorney, Agent, or Firm—Browdy and Neimark

[57] ABSTRACT

In a sample preparation system for iron and steel samples, a grinding machine (1) with a stamping device (2) and/or a cutting machine (3), as well as transport devices (7 to 12), form a modular structural unit for the input, output and transfer of samples. In this case it is possible to connect the stamping device (2) having an integrated robot (20), a sandblasting unit (26), an inductive heating station (27), a sample crusher (25) and a plurality of stamping machines (28, 29, 30) for lollypop samples, and the cutting machine comprising a rotating clamping chuck (31) and an adjustable cutting grinding wheel (32) for cylindrical and conical samples, to a grinding machine (1), which forms the central module and contains a rough and a fine grinding device (18, 20), a cooling device (19) and a clamping device (14) for the samples, and which grinding machine (1) has a dust removal connector (13) for the central removal of dust. The clamping device (14) is embodied in block shape and has two clamping jaws which are movable in respect to each other in two stages.

27 Claims, 3 Drawing Sheets

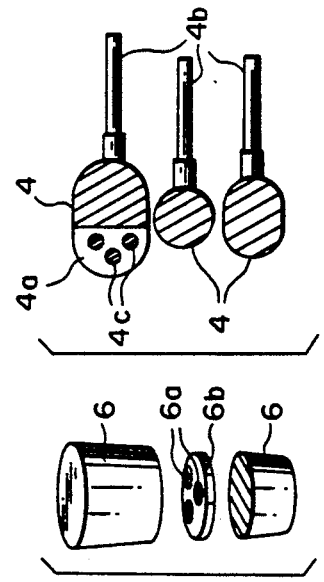
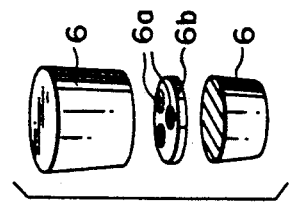
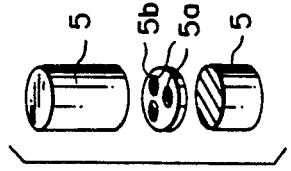
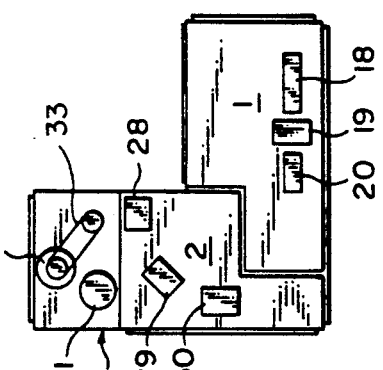
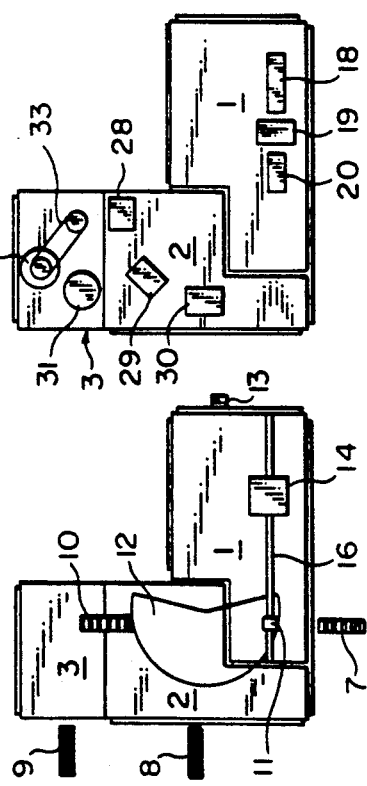
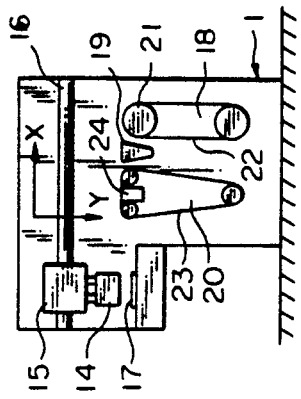
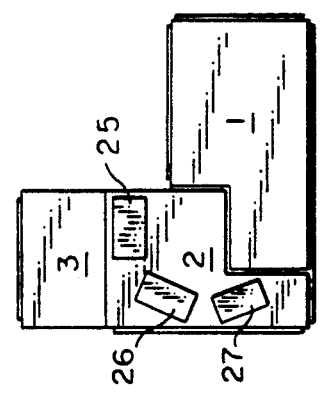
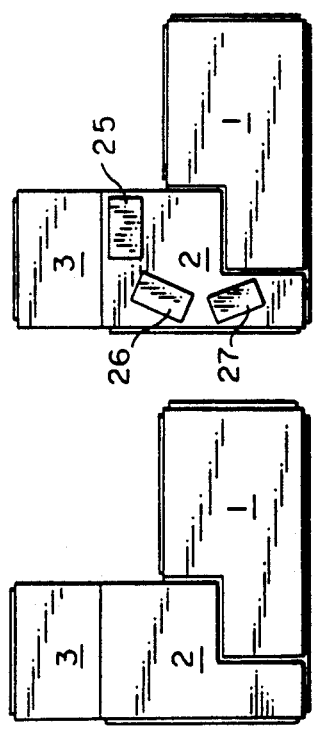

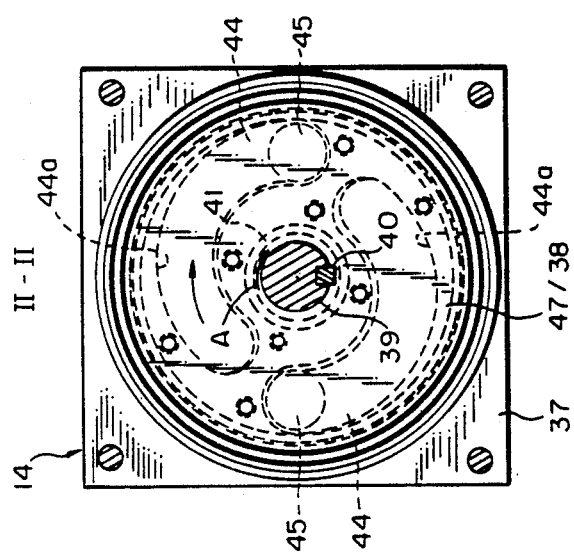
FIG. 13
FIG. 14
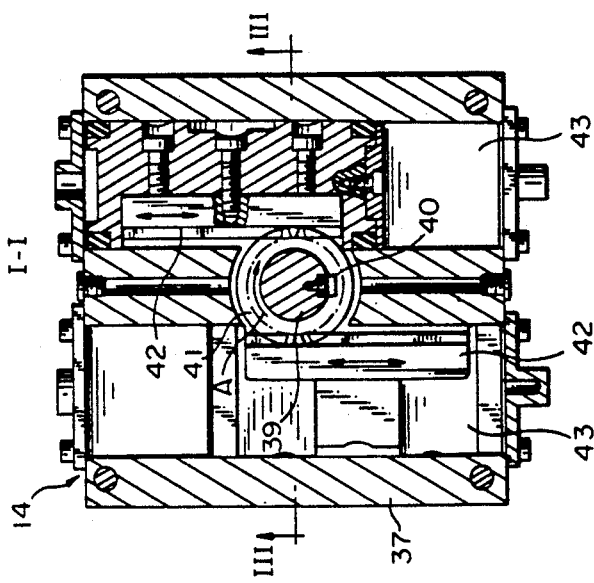
FIG. 12

SAMPLE PREPARATION SYSTEM FOR IRON AND STEEL SAMPLES

BACKGROUND OF THE INVENTION

1. Field of the Invention

The invention relates to a system by means of which iron and steel samples are prepared for sample analysis.

For production control and quality assurance in the steel industry, samples are regularly taken in the course of processing and from the finished products. The chemical composition of these samples is determined by means of optical emission, X-ray fluorescence and combustion analyses.

It should be possible to prepare the samples fully automatically and in a reproducible manner in accordance with the requirements of the analysis apparatus, which might comprise, for example, the generation of a plane surface or the removal of small pieces by stamping.

2. Object of the Invention

It is the object of the invention to provide a sample preparation system for iron and steel samples, where the processing machines to be used for fully automatic and reproducible sample preparation are combined in a variable manner into a fully automatic unit, so that they permit the production of qualitatively perfect samples.

A further object of the invention is seen in the provision of a simply constructed and dependably operating clamping device for the samples, which, with short movement paths and small power expenditure, permits a compact construction with a large clamping range and a great clamping force.

The sample preparation system in accordance with the invention is composed of a modular unit, where it is possible to selectively assign a stamping device and/or a cutting machine to a grinding machine and where the two or three modules for the input and output of samples and transfer of samples are connected by transport systems, which results in the automatic movement of the samples into the preparation system and within the same.

The individual modules are equipped with processing stations, which perform high-quality preparation of the samples.

The grinding machine is furthermore equipped with a compactly built clamping device for the samples to be ground which, with short movement paths and small expenditure of power, has a comparatively large clamping range and great clamping force of its clamping jaws.

The device is simply constructed and operates in two clamping stages. The first clamping stage results in a movement of the clamping jaws towards each other by means of the axial twisting of a clamping disk, and the second clamping stage is attained by applying pressure to the clamping disk. In this way the clamping jaws are first preset to a larger range and subsequently adjusted to a considerably smaller range.

BRIEF DESCRIPTION OF THE DRAWINGS

An exemplary embodiment of the invention is illustrated in the drawings and will be described in detail below.

FIG. 1 is a schematic top view of a modular sample preparation system comprising a grinding machine, a stamping device and a cutting machine, FIG. 2 is a schematic top view of the sample preparation system with sample input and output devices, as well as a sample transfer device and a clamping device, FIG. 3 is a schematic top view of the sample preparation system with processing stations of the lower level of the stamping device, FIG. 4 is a schematic top view of the sample preparation system with processing stations disposed in the upper level, FIG. 5 is a schematic front view of the grinding machine with displaceable clamping device and rough and fine grinding device, FIGS. 6 to 8 show various types of samples, FIG. 12 is a horizontal section through the clamping device in accordance with line I—I of FIG. 9, FIG. 13 is a horizontal section through the clamping device in accordance with line II—II of FIG. 9, FIG. 14 is a lateral view of the clamping device in partial section.

DESCRIPTION OF THE PREFERRED EMBODIMENT

Figure 9:
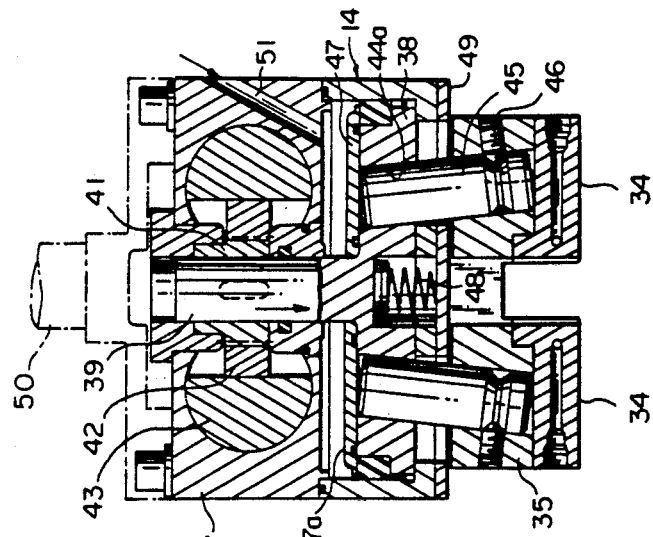
FIG. 9 is a vertical section through the clamping device in accordance with line III—III of FIG. 12, which the clamping jaws in the open position.

The sample preparation systems consists of three modules, a grinding machine (1), a stamping device (2) and a cutting machine (3).

The samples (4, 5, 6) are fed to the system via transport devices (7, 8, 9, 10, 11, 12) and are transferred within the system from one module to the next.

The sample transfer within the preparation system can also be performed by an integrated robot (12). Conveyor belts can be provided as transport devices (7 to 11) for the input and output as well as the transfer of the samples (4 to 6).

The central module is represented by the grinding machine (1), to which can be connected, depending on the type of sample, the stamping device (2) module for lollypop samples (4) (also called lollypop samples) and the cutting machine (3) module for cylindrical and conical samples (5, 6).

Central dust removal of the system is accomplished by means of a dust removal connector (13) of the grinding machine (1), because of which the system can be placed in the immediate vicinity of sensitive analysis apparatus.

The grinding machine (1) has a clamping device (14), which is moved in the X direction by means of a support (15) on guides (16) via a servomotor drive (see FIG. 5).

The clamping device (14) is moved in the Y direction via a second servomotor drive and the guide for this movement is inside the support (15).

The sample (4, 5, 6) is picked up by the clamping device (14) from a sample support (17) and is clamped and pre-ground on a rough grinding device (18). Cooling of the sample (4, 5, 6) takes place subsequently in the cooling device (19) by means of a fluid medium, for example, water. The fine grinding operation on a fine grinding device (20) follows. During this time the sample (4, 5, 6) is additionally cooled by means of a gaseous medium, for example, compressed air. This sequence is controlled by a program. The sequence can be arbitrarily changed by prior settings and in this way adapted to the requirements of the respective sample type.

With samples subject to cracking, a program is selected which pre-cools the sample with compressed air and then cools it down to room temperature with water.

Grinding on the rough grinding device (18) is accomplished by moving the sample (4, 5, 6), which is firmly clamped in the clamping device (14), oscillatingly over a contact wheel (21), around which runs the grinding belt (22). At the same time, this contact wheel (21) drives the grinding belt (22). In the course of the oscillating movement a step-by-step movement in the Y direction is performed until the previously set grinding depth has been reached. This grinding process takes place swiftly (approximately 3 seconds for a usual grinding depth of 0.6 mm). The sample (4, 5, 6) is not in contact with its entire surface, but only with a narrow area of the radius of the contact wheel (21) and thus of the grinding belt (22). This fact prevents excessive heating of the sample (4, 5, 6). Too much heating can have the effect of creating cracks in the surface of the sample or that micro-cracks, which may be present, gape open, so that water can enter in the course of liquid cooling, which has a disadvantageous effect during the subsequent analysis.

It is also possible to use a cup grinding wheel instead of the grinding belt (22) for the rough grinding device (18). This cup grinding wheel is fastened on a vertically extending grinding spindle.

This method is particularly suited for grinding of iron samples because of its long service life.

Grinding on the fine grinding device (20) takes place in that the sample (4, 5, 6), which is firmly clamped in the clamping device (14) is brought above the fine grinding belt (23) and the feed takes place in the Y direction.

In this case a grinding table (24) resiliently seated underneath the grinding belt (23) generates the counter force required for grinding.

This grinding method generates the reproducible surface required for analysis.

The short contact with the grinding belt (23) (approximately 2 seconds) does not cause noticeable heating of the sample (4, 5, 6) and reduces the possibility of material transfer from the remainder of the sample to the surface of the sample (4, 5, 6) to be analyzed.

This fact is of essential importance for unadulterated analysis.

The stamping device (2) has a central robot (12), which transfers the samples (4, 5, 6) to the individual processing stations (25, 26, 27, 28, 29, 30). These processing stations (25 to 30) are arranged in a semi-circle around the robot (12). The robot (12) can pick up the samples (4, 5, 6) from the transport devices (8, 9, 10) and take them out of the system again via the same path.

Transfer of the samples (4, 5, 6) into the grinding machine (1) is accomplished by the transport device (11), which takes the samples (4, 5, 6) from the module 2 to the module 1 (FIG. 2).

On the lower level of the stamping device (2) are disposed processing stations in the form of a sandblasting unit (26), an inductive heating station (27) and a sample crusher (25), and on the upper lever three stamping machines (28 to 30).

The sandblasting unit (26) has two obliquely directed nozzles, which feed the blasting medium in a compressed air stream to the lollypop sample (4a) and remove the scales from it. By means of this, false readings in the combustion analysis are prevented to the greatest extent.

The lollypop sample (4) is inductively heated to 700° to 900° C. in the inductive heating station (27). Because of this it is possible to stamp even steel with a high carbon content and highly alloyed steel.

The robot (12) performs the introduction of the lollypop sample (4a). Overheating of the sample (4a) is prevented by a heat monitoring device.

Iron samples cannot be stamped. To obtain sample pieces for combustion analysis, either the sample itself or a portion thereof is crushed, for which the sample crusher (25) has been provided. The sample pieces to be broken off may be, for example, a cast lollypop (4a) or a sample stem (4b). A tool can be inserted into one of the stamping machines (28, 29 or 30), which breaks off the lollypop (4a) or the stem (4b) from the sample (4). Breaking into small pieces then is performed by the built-in sample crusher (25) into which the lollypop (4a) or the stem (4b) is transferred by the robot (12). The crushing operation is performed between two jaws of hard metal which move towards each other in a circular movement. The drive is hydraulically operated. The gap width of the crusher jaws is adjustable, so that the grain size of the crushed parts can be varied.

The lollypop (4a) is broken off from the sample (4) in the first stamping machine (28). This is necessary in case of lollypop samples (4) if the samples (4) are to be placed into the cassettes of the X-ray fluorescence spectrometer. Sample pieces (4c, 6a, 5a) of 0.5 to 1 g are required for the combustion analysis of carbon, nitrogen and sulfur. For this purpose small rounds (4c, 6a, 6b) are stamped out of the sample disks. The rounds (4c, 6a, 6b) are transported by means of an injector in a pipeline with a gaseous medium to a receptacle device, for example, a reservoir, or directly to the analysis device. The rounds (4c, 6a, 6b) are stamped out in the second stamping machine (29).

The third stamping machine (30) shears off the stem (4b), because the stem (4b) on the sample (4) would make further manipulation difficult. The sheared-off stem (4b) is caught in a collecting hopper.

The cutting machine (3) is used to cut sample disks (5b, 5c) out of cylindrical and conical sample bodies (5, 6) for further processing in the stamping device (2) and the grinding machine (1). The samples (5, 6) are automatically clamped into a rotating clamping chuck (31) and are then cut through with a cutting grinding wheel (32) of the cutting machine (3). A plane surface is generated because of the rotation of the sample (5, 6) during the cutting process. Furthermore, rotation reduces heating of the sample (5, 6), because the cutting grinding wheel (32) is not in contact any farther then the center of the sample (5, 6) and the contact position changes constantly.

The straight cut of this cutting process also makes possible the production of thin sample disks (5b, 6b).

The cutting grinding wheel (32) is seated in an adjustment device (33) by means of which it is possible to even out the wear of the cutting grinding wheel.

The various samples for spectroscopy are shown in FIGS. 6 to 8.

The clamping device (14) in accordance with FIGS. 9 to 14, is in the shape of a block and has two clamping jaws which can be moved in respect to each other in two stages. In this case the two clamping jaws (34) are each fastened on a clamping jaw support (35), with which they are guided in their movements toward or away from each other in a guide (36) underneath the cube-shaped, multiple housing (37) of the clamping device (14).

A clamping disk (38) is seated axially rotatable in the housing (37) and is seated with its rotating shaft (39) in the upper housing area. The rotating shaft (39) is in axial rotational contact with a toothed wheel (41) via a groove-and tongue connector (40) and is provided axially displaceable in a limited range in respect to this toothed wheel (41).

Two toothed racks (42) engage the toothed wheel (41) and are fastened to pressure medium cylinders (43).

Two clamping grooves (44), extending eccentrically around the rotating shaft (40) of the disk, are cut into the clamping disk (38), which are engaged by bolts (45), which are connected with the clamping jaws (34) fixed against movement and which cause the first clamping stage during disk torsion.

In this case the lower longitudinal ends of these bolts (45) have been inserted into the clamping jaw supports (35) and are secured therein by screws (46) or the like. The clamping grooves (44) are cut out of the clamping disk (38) so they extend obliquely, i.e. they extend in the direction of the rotating shaft diverging from each other towards the bottom.

The bolts (45) frictionally engage the clamping grooves (44).

A pressure plate (47) is disposed on the top of the clamping disk (38), which on the one side covers the clamping grooves (44) and with its other side results in a piston surface (47a) which can be put under pressure.

A pressure spring (48) is disposed coaxially with the rotating shaft (40) and is supported on one end on the clamping disk (38) and on the other on an abutment plate (49) disposed between the housing (37) and the clamping jaw supports (35).

The housing (37) of the clamping device (14) is maintained movable in height on the support (15) via vertical telescopic guides (50).

The opened position of the clamping jaws (34) is shown in FIG. 9. As shown in FIG. 12, the toothed racks (42) are extended outwardly in opposite directions by the pressure medium cylinders (43).

FIG. 13 also shows the opened position of the clamping device (14), in which the clamping disk (38) has been twisted into the end position in which the two bolts (45) are located in the ends of the groove which are the farthest from the rotating shaft (39).

The toothed wheel (41), and thus the rotating shaft (40), are turned in the direction of the arrow "A" by the displacement towards each other of the two toothed racks (42) by means of the pressure medium cylinders (43), and the clamping disk (38) is also twisted in the direction of the arrow "A" by this. Because of this the two grooves (44) move around the bolts (45) and in the course of this pull the two bolts (45) towards each other and in the direction of the rotating shaft (39), since the distance of the grooves (44) from the rotating shaft (39) decreases because of the eccentric path of the grooves.

Figure 10:
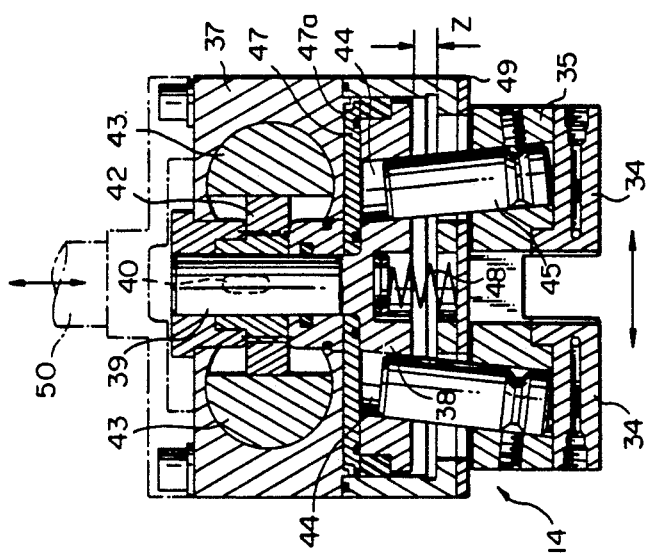
FIG. 10 is a vertical section through the clamping device in the first clamping stage of the clamping jaws.
Figure 11:
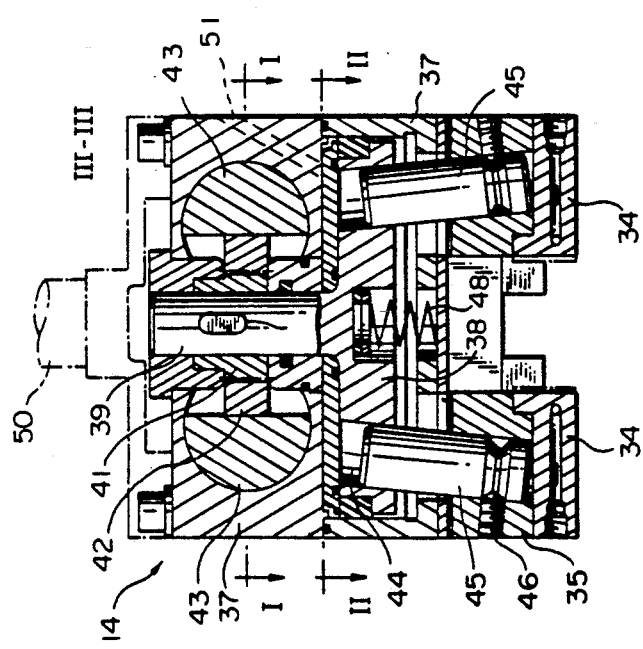
FIG. 11 is a vertical section through the clamping device in the second clamping stage of the clamping jaws.

By means of this the clamping jaw supports (35) and thus the clamping jaws (34) are moved towards each other into the first clamping position in accordance with FIG. 10. In this twisted position of the clamping disk, the other ends of the grooves (44), which are closer to the rotating shaft (39), are located at a distance in front of the bolts (45), looking in the direction of rotation. The rotational angle of the clamping disk (38) is less than 90 degrees.

Subsequently the movement of the clamping jaws (34) into the second clamping position takes place where, through a conduit (51) (pressure medium conduit), a pressure medium is brought to bear on the piston surface (47a) of the pressure plate (47).

The piston surface (47a) is put under pressure and by means of this pressure the clamping disk (38) is downwardly displaced in an axial direction by the amount (Z) in FIG. 10, while the rotating shaft (39) simultaneously can also be axially displaced in respect to the toothed wheel (41) because of the groove-and-tongue connector (40).

In this downward movement of the clamping disk (38), the conical surface (44a) of the clamping disks (44) acts on the bolts (45) and causes further pushing towards each other of the clamping jaws (34) until the bolts (45) ar stopped at the ends of the grooves.

This second clamping path is approximately 1 mm for each clamping jaw (34).

With a stroke of the clamping disk (38) cf approximately 10 mm, the stroke of the clamping jaws of 1 mm each is achieved by means of the conical surface (44a).

The piston surface (47a) is comparatively large and, with a pressure of 4 bar, a clamping force of approximately 8,000 kp is achieved.

A comparatively large clamping path of the clamping jaws, which is up to 30 mm, has been achieved by the axial twisting of the clamping disk (38) and the subsequent displacement of the clamping disk (38).

With decreasing pressure, the pressure spring (48) causes axial return of the clamping disk (38) into the first clamping stage and subsequently the displacement of the toothed racks (42) causes a return of the clamping disk (38) and thus the opening of the clamping jaws (34).

We claim:

1. A preparation system for iron and steel samples, said preparation system comprising: a grinding machine (1), a stamping device (2) and optionally depending on the type of said samples being analyzed, a cutting machine (3), as well as transport devices (7 to 12) for the input, output and transfer between said grinding machine, stamping device and if optionally used said cutting machine of said samples;

wherein housing means for containing each said grinding machine, said stamping device and, if optionally used, said cutting machine engaged together form a single modular structural unit;

said grinding machine having a clamping device (14) and grinding devices (18, 20) for said samples;

wherein said clamping device (14) for said samples is in the shape of a block and has two clamping jaws (34);

said clamping device having means for moving said clamping jaws towards each other in two stages.

2. A preparation system in accordance with claim 1, wherein said clamping device (14) has a clamping disk (38), which is axially rotatable by a pressure medium cylinder (43), toothed racks (42) and a toothed wheel (41), with cut-out clamping grooves (44) extending eccentrically around a rotating shaft (39) of said clamping disk;

said cut-out clamping grooves are engaged by bolts (45), which are fixed against movement to said clamping jaws (34) and which generate a first clamping stage int he course of the twisting of said clamping disk (38); and said clamping disk (38) with said bolts (45) and said clamping jaws (34) being axially displaceable for a second clamping stage by means of pressure form a pressure medium.

3. A preparation system in accordance with claim 1, wherein said two clamping jaws (34) are each fastened on one of two clamping jaw supports (35), together with which said two clamping jaws (34) are movably guided towards and away from each other in a guide (36) underneath a cube-shaped, multiple housing (37) of said clamping device (14).

4. A preparation system in accordance with claim 2, wherein said clamping disk (38) is axially rotatable seated with said rotating shaft (39) in an upper housing area; said clamping disk being secured against torsion and axially displaceable, with said rotating shaft (39) through a tongue-and-groove connection (40) with said toothed wheel (41).

5. A preparation system in accordance with claim 2, wherein two pressure medium cylinders (43) are disposed in an upper area of said housing (37), each of which has a toothed rack (42) interacting with said toothed wheel (41) and which provides an axial twisting of said clamping disk by an opposite movement of said toothed racks (42).

6. A preparation system in accordance with claim 2, wherein said two grooves (44) have been cut into said clamping disk (38) so that they obliquely diverge downwardly and towards the outside, and that they limit, by means of their groove end farthest removed from said rotating shaft (39), the opening position of said clamping jaws (34) and, by means of their groove end located closest to said rotating shaft, the closing position of clamping jaws (34).

7. A preparation system in accordance with claim 2, wherein said two bolts (45) have been inserted into said two clamping jaw supports (35), with their lower longitudinal ends and are secured by means of screws (46) or the like, and that with their upper longitudinal ends they engage said grooves (44) movably and in a frictionally connected manner.

8. A preparation system in accordance with claim 2, wherein a pressure plate (47) is disposed on said clamping disk (38), which covers said clamping grooves (44) and which, for the purpose of an axial displacement of said clamping disk (38), can be put under pressure by a pressure medium fed by a conduit (51) on an upper surface, which forms a piston surface (47a).

9. A preparation system in accordance with claim 2, wherein a pressure spring (48) is disposed coaxially with said rotating shaft (39) of said clamping disk, which on the one end is supported on said clamping disk (38) and on the other end on an abutment plate (49), disposed between said housing (37) and said two clamping jaw supports (35).

10. A preparation system in accordance with claim 2, wherein said clamping grooves (44) forming conical surface (44a) with their outer, obliquely extending groove surfaces, which act on said bolts (45).

11. A preparation system in accordance with claim 1, wherein said clamping device (14) is maintained in a height-adjustable manner via telescopic guides on a support (15) and is movable, together with said support (15), on horizontal guides (16) above said grinding devices (18, 20).

12. A preparation system for iron and steel samples, said preparation system comprising:

a first central module having a housing enclosing therein said grinding machine (1) including a rough grinding device, a fine grinding device (18, 20), at least one cooling device (19) and a clamping device (14) for said samples (4, 5, 6), said first central module joined to a second module having a housing enclosing therein an integrated robot (12), a sandblasting unit (26), an inductive heating station (27), a sample crusher (25) and a plurality of stamping machines (28, 29, 30) comprising a stamping device processing lollypop samples (4) as said samples for analysis, said housing of said first central module joined to said housing of said second module and thereafter optionally joined to a housing of a third module for processing cylindrical and conical samples (5, 6) of said samples for analysis;

said housing of said third module enclosing a cutting station having a cutting machine (3) consisting of a rotating clamping chuck (31) and an adjustable cutting grinding wheel (32) for said processing of cylindrical and conical samples (5, 6) of said samples for analysis:

transport devices for the input, output and transport between said first central module, said second module and if optionally joined, said third module of said samples;

said housing of said first central module, said housing of said second module and said housing of said third module when optionally joined to said housing of said first central module and said housing of said second module forming a modular structural unit; and said grinding machine (1) having a central dust removal connector (13) to serve said modular structural unit.

13. A preparation system in accordance with claim 12, wherein said first module (1) is provided with a first transport device (7) for the input and output of said samples, said plurality of stamping machines is provided with a second transport device (8) for the input and output of said samples and said cutting machine is provided with a third transport device (9) for the input of samples, a fourth transport device (10) is provided between said cutting machine (3) and said plurality of stamping machines and a fifth transport device is provided between said plurality of stamping machines and said grinding machine (1), wherein all transport devices (7, 8, 9, 10, 11) are constituted as conveyor belts.

14. A preparation system in accordance with claim 12, wherein said clamping device (14) for said samples (4, 5, 6) in said grinding machine (1) is movable in a horizontal and a vertical direction.

15. A preparation system in accordance with claim 12, wherein said rough grinding device and said fine grinding device (18, 20) have endless, rotating grinding belts (22, 23), said rough grinding device (18) having means for oscillatingly moving said samples (4, 5, 6) over a first of said rotating grinding belts (22), driven by a contact wheel (21), and means for simultaneously feeding said samples in steps to a grinding depth, and, while feeding to said grinding depth, being held in said fine grinding device (20) against a second of said grinding belts (23) and a grinding table (24), resiliently seated under said one of said grinding belts.

16. A preparation system in accordance with claim 12, wherein said rough grinding device (18) has a cup grinding wheel fastened to a vertical grinding spindle.

17. A preparation system in accordance with claim 12, wherein said clamping device (14) for said samples is in the shape of a block and has two clamping jaws (34);

said clamping device having means for moving said clamping jaws towards each other in two stages.

18. A preparation system in accordance with claim 12, wherein said clamping device (14) has a clamping disk (38), which is axially rotatable via a pressure medium cylinder (43), toothed racks (42) and a toothed wheel (41), with cut-out clamping grooves (44) extending eccentrically around a rotating shaft (39) of said clamping disk;

said cut-out clamping grooves are engaged by bolts (45), which are fixed against movement to said clamping jaws (34) and which generate a first clamping stage in the course of the twisting of said clamping disk (38); and said clamping disk (38) with said bolts (45) and a said clamping jaws (34) being axially displaceable for a second clamping stage by means of pressure from a pressure medium.

19. A preparation system in accordance with claim 17, wherein said two clamping jaws (34) are each fastened on one of two clamping jaw supports (35), together with which said two clamping jaws (34) are movably guided towards and away from each other in a guide (36) underneath the cube-shaped, multiple housing (37) of said clamping device (14).

20. A preparation system in accordance with claim 18, wherein said clamping disk (38) is axially rotatable seated with said rotating shaft (39) in an upper housing area;

said clamping disk being connected, secure against torsion and axially displaceable, with said rotating shaft (39) through a tongue-and-groove connection (40) with said toothed wheel (41).

21. A preparation system in accordance with claim 18, wherein two pressure medium cylinders (43) are disposed in an upper area of said housing (37), each of which has a toothed rack (42) interacting with said toothed wheel (41) and which provides an axial twisting of said clamping disk by an opposite movement of said toothed racks (42).

22. A preparation system in accordance with claim 18, wherein said two grooves (44) have been cut into said clamping disk (38) so that they obliquely diverge downwardly and towards the outside, and that they limit, by means of their groove end farthest removed from said rotating shaft (39), the opening position of said clamping jaws (34) and, by means of their groove end located closest to said rotating shaft, the closing position of clamping jaws (34).

23. A preparation system in accordance with claim 18, wherein said two bolts (45) have been inserted into said two clamping jaw supports (35), with their lower longitudinal ends and are secured by means of screws (46) or the like, and that with their upper longitudinal ends they engage said grooves (44) movably and in a frictionally connected manner.

24. A preparation system in accordance with claim 18, wherein a pressure plate (47) is disposed on said clamping disk (38), which covers said clamping grooves (44) and which, for the purpose of an axial displacement of said clamping disk, can be put under pressure by a pressure medium fed by a conduit (51) on an upper surface, which forms a piston surface (47a).

25. A preparation system in accordance with claim 18, wherein a pressure spring (48) is disposed coaxially with said rotating shaft (39) of said clamping disk, which on the one end is supported on said clamping disk (38) and on the other end on an abutment plate (49), disposed between said housing (37) and said two clamping jaw supports (35).

26. A preparation system in accordance with claim 18, wherein said clamping grooves (44) form a conical surface (44a) with their outer, obliquely extending groove surfaces, which act on said bolts (45).

27. A preparation system in accordance with claim 12, wherein 27 said clamping device (14) is maintained in a height-adjustable manner via telescopic guides on a support (15) and is movable, together with said support (15), on horizontal guides (16) above said grinding devices (18, 20).

* * * * *